US00PP13978P29

(12) United States Plant Patent
Olsthoorn

(10) Patent No.: US PP13,978 P2
(45) Date of Patent: Jul. 15, 2003

(54) SPATHIPHYLLUM PLANT NAMED 'SWEET CLAUDIO'

(75) Inventor: Petrus C. M. Olsthoorn, Monster (NL)

(73) Assignee: Pothos Plant B.V., Honselersdijk (NL)

( * ) Notice: Subject to any disclaimer, the term of this patent is extended or adjusted under 35 U.S.C. 154(b) by 0 days.

(21) Appl. No.: 10/076,533

(22) Filed: Feb. 19, 2002

(51) Int. Cl.[7] ..... A01H 5/00
(52) U.S. Cl. ..... Plt./364
(58) Field of Search ..... Plt./364

(56) References Cited

PUBLICATIONS

UPOV–ROM GTITM Computer Database 2002/03, GTI Jouve Retrieval Software, Citation for Spathiphyllum 'Sweet Claudio'.*

* cited by examiner

*Primary Examiner*—Bruce R. Campell
*Assistant Examiner*—June Hwu
(74) *Attorney, Agent, or Firm*—Foley & Lardner

(57) ABSTRACT

A new and distinct Spathiphyllum plant named 'Sweet Claudio' characterized by its dark and glossy leaves, large spadix, most shoots producing inflorescences, and dark inflorescence stem.

2 Drawing Sheets

Latin name of the genus and species of the plant claimed: Spathiphyllum hybrid.

Variety denomination: 'Sweet Claudio'.

BACKGROUND OF THE INVENTION

The present invention relates to a new and distinct cultivar of Spathiphyllum plant, hereinafter referred to by the cultivar name 'Sweet Claudio'.

The new cultivar originated from a cross made in a controlled breeding program in Monster, The Netherlands. The female parent is '91274-26' (unpatented). The male parent is '93161-95' (unpatented). 'Sweet Claudio' was discovered and selected by the inventor, Petrus C. M. Olsthoorn, as a flowering plant within the progeny of the stated cross in a controlled environment in Monster, The Netherlands.

Asexual reproduction of the new cultivar was first performed by tissue culture in week 16 of 1997 in Honselersdijk, The Netherlands and has demonstrated that the combination of characteristics as herein disclosed for the new cultivar are firmly fixed and retained through successive generations of asexual reproduction and reproduces true-to-type.

BRIEF DESCRIPTION OF THE INVENTION

The following traits have been repeatedly observed and are determined to be basic characteristics of 'Sweet Claudio' which in combination distinguish this Spathiphyllum as a new and distinct cultivar:

1. Dark and glossy leaves;
2. Large spadix;
3. Most shoots producing inflorescences; and
4. Dark inflorescence stem.

'Sweet Claudio' has not been observed under all possible environmental conditions. The phenotype of the new cultivar may vary significantly with variations in environment such as temperature, light intensity, and day length without any change in the genotype of the plant. The following observations, measurements and values describe the new cultivar as grown in Honselersdijk, The Netherlands under conditions which closely approximate those generally used in commercial practice.

Of the many commercial cultivars known to the present inventor, the most similar in comparision to 'Sweet Claudio' is the cultivar 'Cupido' (unpatented). 'Sweet Claudio' has darker and glossier leaves than 'Cupido'. The inflorescence of 'Sweet Claudio' is a rounder than the inflorescence of 'Cupido'. The plant height of 'Sweet Claudio' is approximately 10 percent less than that of 'Cupido'. The main vein color of 'Sweet Claudio' is lighter than the main vein color of 'Cupido'. The inflorescences of 'Sweet Claudio' are somewhat shell-shaped whereas the inflorescences of 'Cupido' are more oval. The spadix of the inflorescence of 'Sweet Claudio' is 10 to 15 percent bigger than the spadix of the inflorescence of 'Cupido'. The inflorescence stem is darker than the inflorescence stem of 'Cupido'. Most shoots of 'Sweet Claudio' produce inflorescences whereas only the main shoots of 'Cupido' produce inflorescences. 'Cupido is' more sensitive to light than 'Sweet Claudio', causing the leaves of 'Cupido' to turn lighter faster. Finally, in order to get the shoots of Spathiphyllum into flowering gibberalic acid is added. 'Cupido' needs more than twice the concentration of this hormone than 'Sweet Claudio' to get the same result.

BRIEF DESCRIPTION OF THE DRAWINGS

The accompanying photographic drawings show a 30-week old plant of 'Sweet Claudio'.

The first drawing shows a 'Sweet Claudio' plant on the left and a close up of its inflorescence on the right.

The second drawing shows a 'Sweet Claudio' plant on the left with a 'Cupido' plant on the right.

DETAILED BOTANICAL DESCRIPTION

The following observations, measurements and values describe the new cultivar at 30-weeks as grown in Honselersdijk, The Netherlands under conditions which closely approximate those generally used in commercial practice. Grown in standard glasshouses in well-drained cocos, pH values in cocos/peat soil (50/50) is 6.0–6.2 and 5.8–6.0 in potting soil. Base fertilizing (PG-mix) is 0.75 kgs in cocos/peat soil as well as in potting soil. This species needs careful fertilizer treatment; mixes of calcium nitrate, iron chelate (EDDHA and DTPA), magnesium sulphate, mono potassium phosphate, potassium nitrate, borax, manganese, molybdenum and copper sulphate. Ideal growing conditions under which this plant is grown is 21–23 degrees Celsius during the day and 20 degrees Celsius at night. For flower initiation 'Sweet Claudio' gets 60 ppm of gibberalic acid (depending on the pot size, plant development and age of plant).

Color references are made to The Royal Horticultural Society Colour Chart (R.H.S.), except where general colors of ordinary significance are used. Color values were taken under daylight conditions at approximately noon in Boskoop, The Netherlands.

Origin: Homselersdijk, The Netherlands, November 2001.
Parentage:
*Male parent.*—'91274-26'.
*Female parent.*—'93161-95'.
Classification:
*Botanical.*—Spathiphyllum.
*Commercial.*—Spathiphyllum cv. Sweet Claudio.
Propagation: By tissue culture.
Plant:
*Appearance.*—Broad upright with leaf petioles growing directly from base.
*Height.*—Average 75 cm.
*Width.*—Average 75 cm.
*Growth habit.*—Moderately vigorous.
*Time of flowering.*—18 weeks after potting of a 20 cm cutting.
*Winter hardiness.*—USDA Zone 10.
*Stems.*—Leaves grow directly from base, so no stems are visible.
*Roots.*—Time to initiate roots: 1–2 weeks under 21–23 degrees Celsius (day) and 20 degrees Celsius at night. Time to develop roots: 3–4 weeks under 21–23 degrees Celsius (day) and 20 degrees Celsius at night. Rooting habit: Freely branching.
Foliage:
*Shape.*—Narrow elliptic to lanceolate.
*Apex.*—Acute to slightly apiculate, often twisted due to wavy margin.
*Base.*—Attenuate.
*Texture.*—Smooth, glossy, somewhat leathery.
*Leaf color.*—Upper surface: Green, closest to but darker than RHS 139A. Lower surface: Green RHS 137A to RHS 137B.
*Midrib color.*—Upper surface: Green RHS 143A to RHS 143B. Lower surface: Yellow-green RHS 144B.
*Size of leaf.*—Width: Average 10.8 cm. Length: Average 38 cm. Petiole: Average length 35 cm, average diameter 4 mm, rounded, green in color RHS 143A.
*Petiole sheath.*—Average 23 cm long and 5 mm wide (measured at halfway point).
*Geniculum.*—Average length 3.9 cm, average width 5.5 mm, green in color RHS 143C.
*Veins.*—Average 12 pairs of furrowed secondary veins, upper side color green RHS 143A to RHS 143B, under side color yellow-green RHS-144A.
Inflorescence description:
*Immature.*—Peduncle: Average length 57 cm, average diameter 4 mm, rounded, green in color RHS 143A to RHS 143B. Spathe: Average length 15 cm, average width 6.2 cm, cupped, average depth 1.2 cm.
*Mature.*—Spathe: Size: Average length 16.5 cm, average width 6.9 cm, cupped, average depth 1.2 cm. Color: Unopened Bud: White, closest in color between RHS 155A and RHS 157D. Fully Open: Front Surface: White, closest to RHS 155A, midrib green; RHS 142D. Back Surface: White, closest to RHS 155A, midrib green RHS 143B to RHS 143C. Apex: Apiculate, green RHS 143A to RHS 143D. Faded: Front Surface: Brown RHS 199A. Back Surface: Brown RHS 199A to RHS 199B. Apex: Brown RHS 199A to RHS 199B.
*Arrangement.*—Solitary.
*Shape.*—Broad lanceolate, base decurrent.
*Margins.*—Entire.
*Fragrance.*—Sweet.
*Lastingness of the individual inflorescence.*—On average over two weeks.
Reproductive organs:
*Spadix.*—Size: Average length 6 cm, average width 1.3 cm. Quantity: Average 150 individual flowers per spadix. Color: Greyed-yellow RHS 160C. Stamens: 6, pressed against styles. Pistil: Each individual flower has one pistil with a tri-parted stigma; the pistil has an average length of 2 mm and is greyed-yellow in color RHS 160C to RHS 160D.
*Pollen.*—Yellow-white RHS 158A
Seed production: No observations to date.
Fruit production: No observations to date.
Disease resistance/susceptibility: No observations to date.

I claim:

1. A new and distinct Spathiphyllum plant named 'Sweet Claudio', substantially as illustrated and described herein.

* * * * *

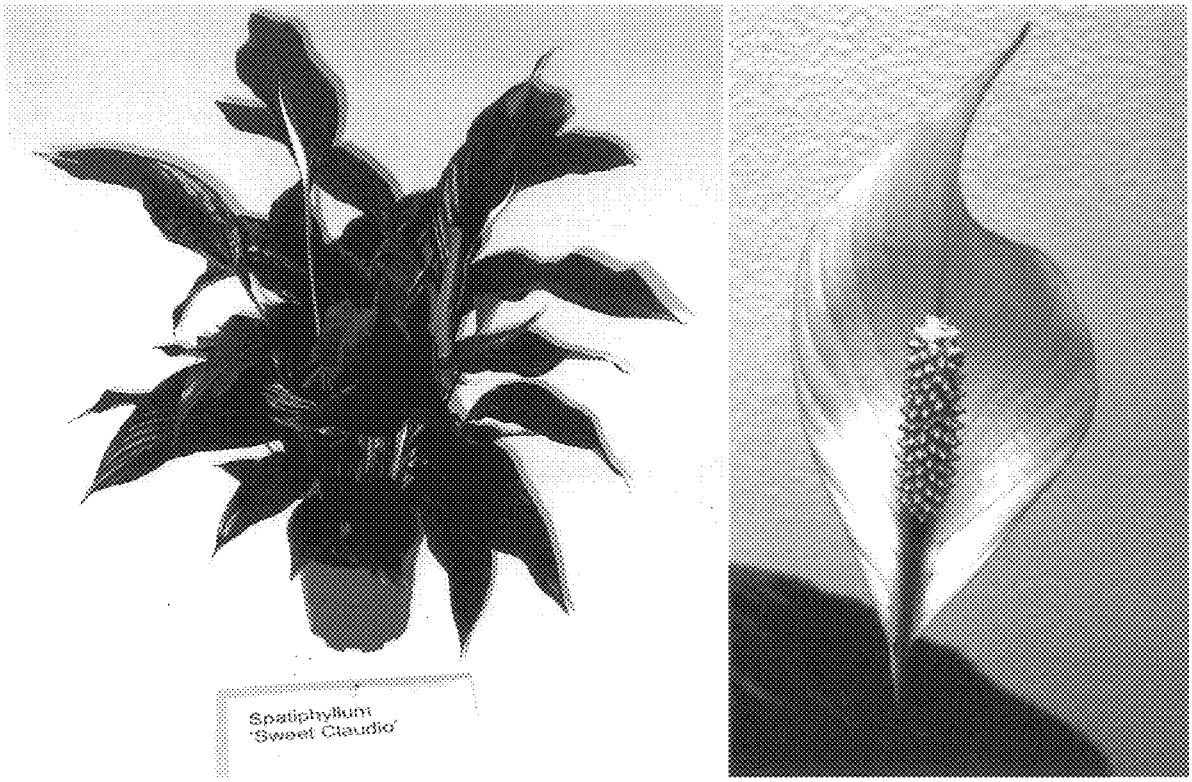
Spatiphyllum
'Sweet Claudio'

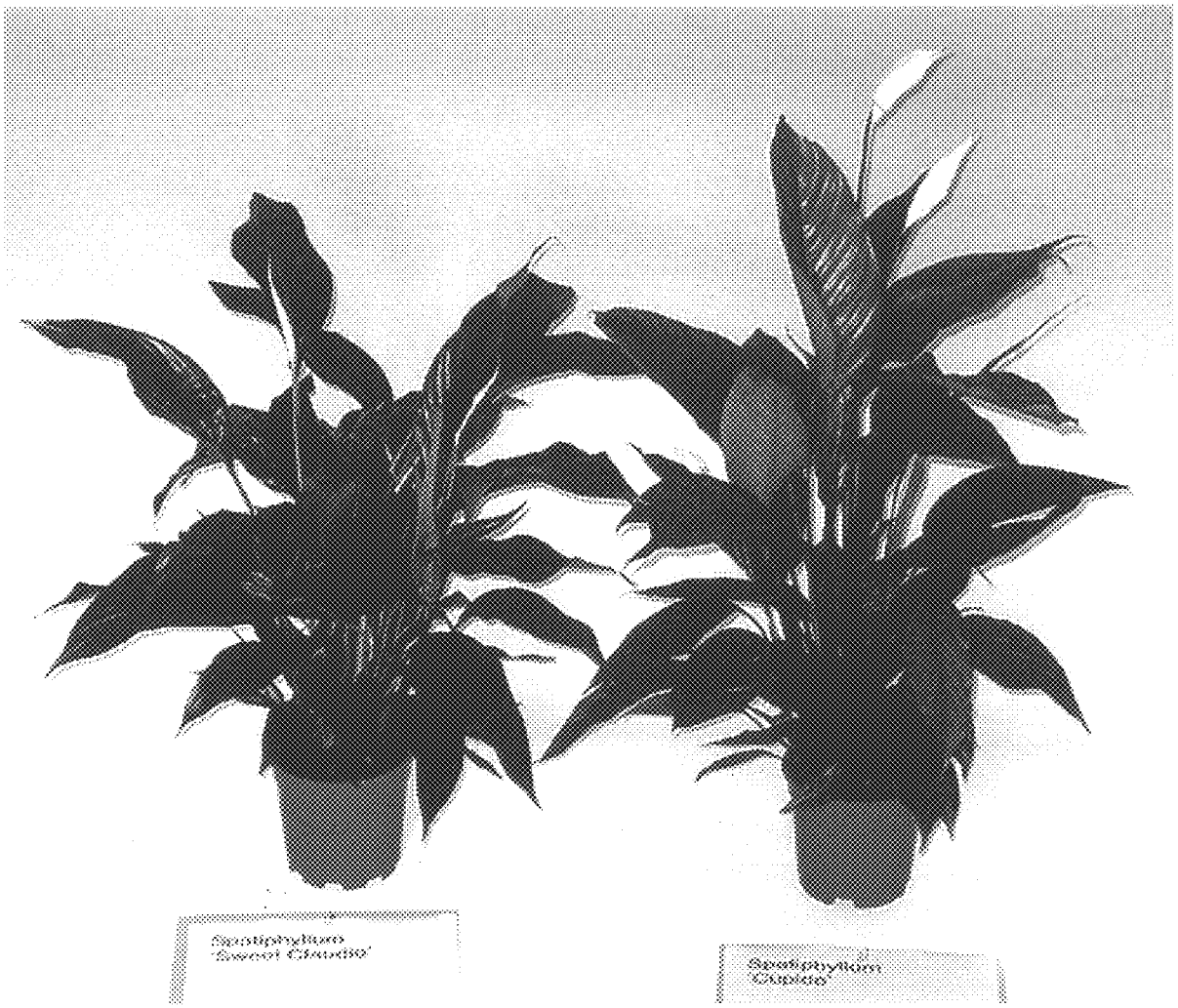
Spathiphyllum
'Sweet Cloudia'
Spathiphyllum
'Cupido'